United States Patent [19]

Ekramoddoullah

[11] Patent Number: 5,686,249
[45] Date of Patent: Nov. 11, 1997

[54] TEST FOR DETERMINING FROST HARDINESS OF CONIFER SEEDLINGS AND PROTEIN AND ANTIBODY RELATED THERETO

[75] Inventor: Abul K. M. Ekramoddoullah, Victoria, Canada

[73] Assignee: Forestry Canada, Hull, Canada

[21] Appl. No.: 338,127

[22] Filed: Nov. 9, 1994

[51] Int. Cl.$^6$ .................. G01N 33/53; C07K 16/00; C07K 14/415; A01H 7/00
[52] U.S. Cl. .................. 435/7.1; 435/7.92; 435/975; 530/387.1; 530/350; 800/200; 800/DIG. 51
[58] Field of Search .................. 435/7.1, 7.92, 435/975; 530/350, 387.1; 800/200, DIG. 51

[56] References Cited

PUBLICATIONS

Yacoob RK & Filion WG. (1987) Biochem. Cell Biol. 65: 112–119.
Ekramoddoullah; et al—"Changes in protein profile of . . . "—Cdn. Journal of Plant Pathology 15:259–264 1993.
Ekramoddoullah—"Analyses of Proteins of Western White Pine Needles"—pp. 102–108 3rd IUFRO Rusts of Pine Working Party Con. 1989.
Ekramoddoullah—"An innovative approach to the Determination . . . " The Faseb Journal, Vo. 6, Nos. 4&5, Mar. 1992.
Ekramoddoullah—"Analysis of needle proteins and N-terminal amino acid . . . "—Tree Physiology 12, 101–106 1993.
Ekramoddoullah—"Monoclonal antibodies and their application in forestry"—Meeting of IUFRO Working Party S2.07–09, Canada, 1990.

*Primary Examiner*—Lila Feisee
*Assistant Examiner*—John Lucas

[57] ABSTRACT

A method of determining frost hardiness of a conifer seedling, which comprises detecting an amount of a cold protein in tissue of said conifer, the cold protein being a protein of approximately 19 kD that increase significantly in amount in the conifer during fall season (autumnal) months and that imparts frost hardiness to the seedling, and then assessing frost hardiness based on said detected amount. In the case of *Pinus lambertiana*, the cold protein includes the N-terminal sequence: Val—Ser—Gly—Thr—Ser—Ser—Thr—Glu—Glu—Val—Val—Gln—Asn—Glu—Ala—Arg—Arg—Leu—Trp—Asn [SEQ ID NO:1]; and in the case of *Pinus monticola*, the cold protein includes the N-terminal sequence: Val—Ser—Gly—Thr—Ser—Ser—Thr—Glu—Glu—Val—Val—Gln—Val—Glu—Ala—Arg—Arg—Leu—Trp—Asn—Ala—Thr—Thr—Lys—Asp [SEQ ID NO:3]. The invention also relates to conjugates and antibodies used in the method.

10 Claims, 5 Drawing Sheets

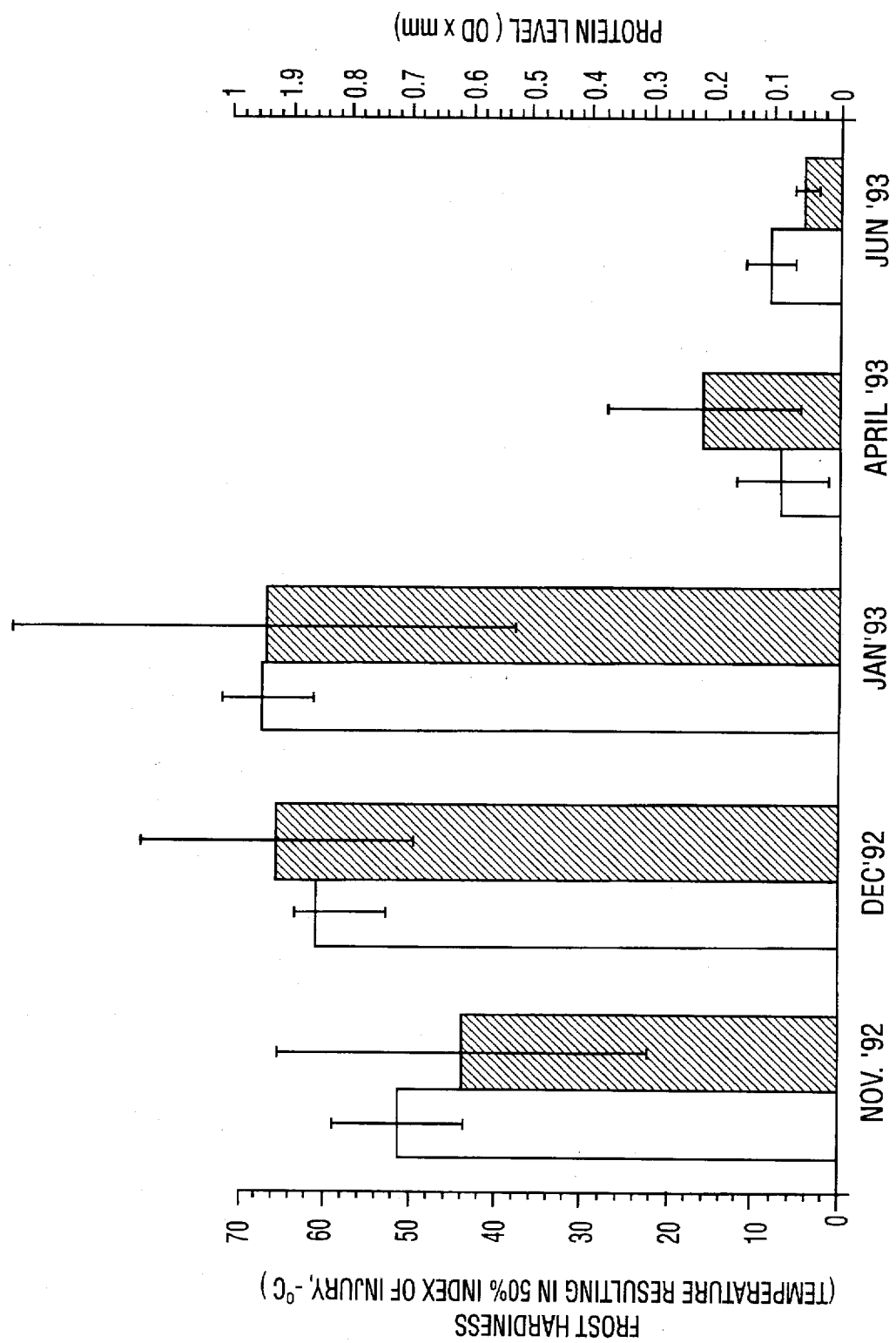

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Pinus lambertiana
    ( B ) STRAIN: Dougl.
    ( F ) TISSUE TYPE: Leaf ( x i ) SEQUENCE DESCRIPTION: SEQ ID NO:1:

Val Ser Gly Thr Ser Ser Thr Glu Glu Val Val Gln Asn Glu Ala Arg
1               5                   10                  15

Arg Leu Trp Asn
            20

( 2 ) INFORMATION FOR SEQ ID NO:2:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Pinus Lambertiana
        ( B ) STRAIN: Dougl.
        ( F ) TISSUE TYPE: Leaf ( x i ) SEQUENCE DESCRIPTION: SEQ ID NO:2:

Val Ser Gly Thr Ser Ser Thr Glu Glu Val Val Gln Asn Glu Ala Arg
1               5                   10                  15

Arg Cys ( 2 ) INFORMATION FOR SEQ ID NO:3:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Pinus monticola
        ( B ) STRAIN: D. Don
        ( F ) TISSUE TYPE: Leaf ( x i ) SEQUENCE DESCRIPTION: SEQ ID NO:3:

Val Ser Gly Thr Ser Ser Thr Glu Glu Val Val Gln Val Glu Ala Arg
1               5                   10                  15

Arg Leu Trp Asn Ala Thr Thr Lys Asp
            20                  25

TEST FOR DETERMINING FROST HARDINESS OF CONIFER SEEDLINGS AND PROTEIN AND ANTIBODY RELATED THERETO

BACKGROUND OF THE INVENTION

I. Field of the Invention

This invention relates to tests for determining frost hardiness (resistance to damage by freezing temperatures) in conifer seedlings, and to proteins and antibodies related to such tests.

II. Description of the Prior Art

Most temperate-zone perennial plants go through an annual cycle of a growing phase in summer and a dormant phase in winter (Lavender 1985, see the "References" section at the end of this disclosure, Ref. No. 40). Following environmental cues such as lower temperatures and shorter photoperiods, plants undergo several physiological changes including the development of frost hardiness. Frost hardiness is a mechanism which plants have evolved to maintain adequate freezing tolerance during cold weather and to resume growth when the risk of freezing has passed (Guy 1990, Ref. No. 25). Thus arctic plants tend to be more frost hardy than subarctic plants, but frost hardiness significantly increases in plants from both locations with lower temperature (Robberecht and Junttila 1992, Ref. No. 51).

Over 730 million forest tree seedlings are planted annually in Canada to ensure sustainable timber harvests. As a planting strategy, it is a common practice to develop frost hardiness of conifer seedlings by inducing dormancy in them. If a 10% increase in the survival rate of planted seedlings can be induced in this way, a conservative estimate indicates a resulting annual benefit to the forest industry of $30 million (Canadian). Unfortunately, there is no precise way of selecting seedlots well suited for planting sites having specific frost problems (e.g. late spring frost, or summer frosts) or of selecting seedlots for planting sites within a particular biogeoclimatic zone when such seedlots originate from regions outside that zone.

The dormancy condition of conifer seedlings stock prior to lifting and cold storage is currently assessed using the $-18°$ C. freeze test. In this procedure, the seedlings are frozen at $-18°$ C., then placed in a chamber containing a controlled environment for 7 days, at which time the foliage is visually assessed for damage.

The limitations of the conventional frost hardiness test are that (i) it takes a week to perform the test, (ii) the assessment is not precise, and (iii) the test is labor-intensive.

A positive correlation of the expression of cold-regulated genes with freezing tolerance has been observed in several plants (Mohapatra et al. 1989, Ref. No. 46; Houde et al. 1992, Ref. No. 32; Binh and Oono 1992, Ref. No. 5). Consistent with these findings, changes in protein synthesis have also been positively correlated with frost hardiness (Kang and Titus 1980, Ref. No. 37; Pomeroy and Siminovitch 1970, Ref. No. 50). Cold acclimation is closely paralleled by an accumulation of membrane-bound proteins in the leaves of Korean boxwood (Gusta and Wesser, 1992, Ref. No. 23). Crude protein extracts obtained from cold-acclimated leaves of spinach and also some galactose specific lectins have been shown to protect isolated thylakoid membranes against freeze-thaw damage (Hincha et al. 1989, Ref. No. 27; 1990, Ref. No. 28; 1993, Ref. No. 29). Removal of apoplastic proteins that were accumulated during cold acclimation of leaves of winter rye increased the level of injury of these leaves caused by freezing (Marentes et al. 1993, Ref. No. These workers suggested that the apoplastic proteins might have ice nucleating and antifreeze properties of controlling extracellular ice formation in leaf tissues, a mechanism thought to operate in insects and marine invertebrates (Storey and Storey 1988, Ref. No. 58; Dunman et al. 1991, Ref. No. 12). It has been reported (Kurkela and Franck 1990, Ref. No. 38) that a cold regulated gene from a plant, *Arabidopsis thaliana* encodes a protein having amino acid sequence homology with certain fish antifreeze proteins.

Some polypeptides encoded by cold-regulated genes are of low molecular weights (Johnson-Flanagen and Singh 1987, Ref. No. 36) and have unusual properties of remaining soluble upon boiling (Lin et al. 1990, Ref. No. 41; Lin and Thomashow 1992, Ref. No. 42). During cold acclimation and decrease in photoperiod, there are also changes in other protein synthesis (Roberts et al. 1991, Ref. No. 52; Thomashow et al. 1990, Ref. No. 60; Voinikov and Korytov 1970), Ref. No. 63; Weiser 1970, Ref. No. 64; Weiser et al. 1990, Ref. No. 65; Wetzel and Greenwood 1991, Ref. No. 68; Wetzel et al. 1989, Ref. No. 66; Wetzel and Greenwood 1989, Ref. No. 67; Saueter and Cleve 1993, Ref. No. 56; Saez-Vasquez et al. 1993, Ref. No. 53; Zhu et al. 1993, Ref. No. 69; Coleman et al. 1991, Ref. No. 7; 1992, Ref. No. 8; 1993, Ref. No. 9), some of which serve to produce storage proteins, storing nitrogen over the winter which will then be mobilized for new growth in the spring (Roberts et al. 1991, Ref. No. 52; Wetzel and Greenwood 1991, Ref. No. 68; Wetzel et al. 1989, Ref. No. 66; Wetzel and Greenwood 1989, Ref. No. 67). Cold acclimation has also been associated with increased levels of enzyme systems of antioxidant systems of some plant species (Esterbauer et al. 1980, Ref. No. 20; Nakagawara and Sagisaka 1984, Ref. No. 47; Schoner et al. 1989, Ref. No. 57; de Kok and Oosterhuis 1983, Ref. No. 11; Esterbauer and Grill, 1978, Ref. No. 19; Guy and Carter 1984, Ref. No. 24; Sagisaka 1985, Ref. No. 54; Asada and Takahasi 1987, Ref. No. 3; Schoner et al. 1989, Ref. No. 57; Anderson et al. 1992, Ref. No. 2). It was also shown that the level of certain heat-shock proteins increased with cold acclimation (Neven et al. 1992, Ref. No. 48). The induction of similar stress-related proteins has also been shown in some plant species during exposure to heat (Vierling and Nguyen, 1992, Ref. No. 62), salinity (Hofner et al., 1987, Ref. No. 31; Hanson, 1992, Ref. No. 26), and drought (Close et al. 1989, Ref. No. 6), and in seeds during maturation drying (Bewley and Oliver, 1992, Ref. No. 4).

However, no molecular markers positively associated with frost hardiness are presently available, so seedlots cannot currently be selected on the basis of the presence or absence of such markers.

Considering the narrow window available for lifting the seedlings, the present method of determining frost hardiness is time consuming and also not precise. Accordingly, there is a need for an improved method of determining frost hardiness in conifer seedlings and an improved method of protecting such seedlings and other plants against frost.

SUMMARY OF THE INVENTION

An object of the present invention is to provide an improved test for assessing frost hardiness in conifer seedlings.

Another object of the present invention is to enable frost hardiness tests to be carried out quickly and reliably.

Another object of the invention is to use such frost hardiness tests to develop planting procedures and methods.

The present invention is based on the identification and characterization of a cold protein, or close homologues, in three white pines, namely sugar pine (*Pinus lambertiana*), eastern white pine (*Pinus strobus*) and western white pine (*Pinus monticola*), and its association with frost hardiness. These findings have been used to develop an immunochemical method to determine frost hardiness in conifer seedlings.

More specifically, according to the invention, there is provided a method of determining frost hardiness of a conifer seedling, which comprises detecting an amount of a cold protein in tissue of said conifer, said cold protein being a protein of approximately 19 kD that increase significantly in amount in said conifer during fall season (autumnal) months and that imparts frost hardiness to said seedling, and assessing frost hardiness based on said detected amount.

In the case of *Pinus lambertiana*, the cold protein includes the N-terminal sequence: Val—Ser—Gly—Thr—Ser—Ser—Thr—Glu—Glu—Val—Val—Gln—Asn—Glu—Ala—Arg—Arg—Leu—Trp—Asn [SEQ ID NO:1].

This protein sequence has been recorded with the Protein Identification Resource Database (PIR) of the National Biomedical Research Foundation, Georgetown University Medical Centre, 3900 Reservoir Road, Washington D.C. 20007-2195, under Accession No. A40451, since about Dec. 30, 1991.

In the case of *Pinus monticola*, the cold protein includes the N-terminal sequence: Val—Ser—Gly—Thr—Ser—Ser—Thr—Glu—Glu—Val—Val—Gln—Val—Glu—Ala—Arg—Arg—Leu—Trp—Asn—Ala—Thr—Thr—Lys—Asp [SEQ ID NO:3].

In the case of other Pinus species, the cold protein contains an homologue (at least 80% similarity) of the N-terminal sequences shown above.

The invention also relates to the proteins themselves, protein conjugates used for producing antibodies capable of binding to the proteins for identification, the antibodies thus produced, and methods of using the proteins and antibodies for determining frost hardiness of seedlings.

BRIEF DESCRIPTION OF THE DRAWINGS

FIG. 7 shows the seasonal variation in the frost hardiness and the level of cold protein of two-year old western white pine seedlings. Seedlings were kept outdoors. Foliage was harvested from ten seedlings separately at different times as indicated. The frost hardiness (open bar) of leaves and their content of cold-protein (hatched bar) are plotted. Error bars represent standard deviation of the mean of ten seedlings.

DETAILED DESCRIPTION OF THE INVENTION

Figure 1:
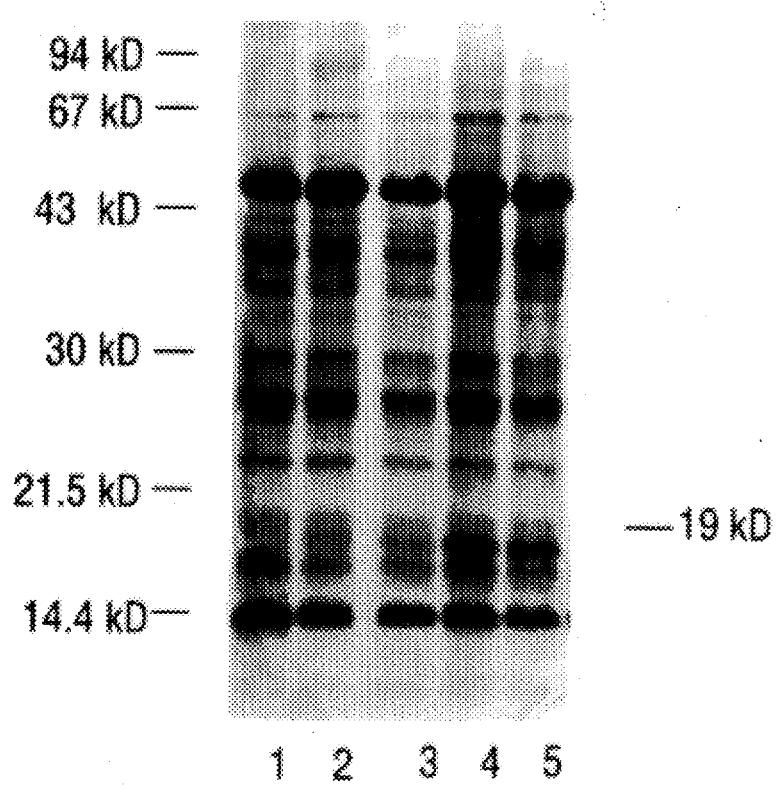
FIG. 1 is a one dimensional SDS-PAGE analysis of sugar pine foliar proteins as explained in the Experimental Detail below. This electrophorogram was obtained from seedlings of seedlot ZL. A similar electrophorogram was obtained with seedlings of the other seed lot. Lanes 1–5 are samples collected on October 5, October 11, October 20, November 15, and November 28, of the same year, respectively. Positions of standard molecular weight markers are indicated on the left side and the position of the 19 kD band is shown on the right.

During an investigation of the changes in the synthesis of proteins of sugar pine following inoculation with a fungal patbogen (Ekramoddoullah and Hunt 1993, Ref. No. 17), a protein was detected in increasing amounts in the fall season (autumnal months) in all seedlings tested.

This protein, designated Pin l, 1 was found to be an approximately 19 kD protein that was present in increasing amounts in samples collected as fall progressed but could not be detected in samples collected the following summer. Because young seedlings were used in the experiments, it was initially thought that the detected protein was associated with the developmental stages of the seedlings. However, this protein was also detected in the secondary foliage of two-year-old seedlings (but only in samples collected in winter months). Thus, considering the shorter daylength and lower temperature in the fall, the synthesis of this protein was considered to be environmentally regulated.

The present invention is based on the characterization of this protein, strategies of producing a specific antibody to the protein, immunochemical detection of homologous proteins in other conifers, specifically in eastern and western white pine, and the positive association of the protein with frost hardiness of conifer foliage.

The protein detected in sugar pine is composed of two acidic isoforms and amino acid sequence analysis has revealed that the two isoforms have an identical amino terminal amino acid sequence, namely the sequence: Val—Ser—Gly—Thr—Ser—Ser—Thr—Glu—Glu—Val—Val—Gln—Asn—Glu—Ala—Arg—Arg—Leu—Trp—Asn [SEQ ID NO:1]

The timing of accumulation of the 19 kD protein in sugar pine foliage is reminiscent of the accumulation of vegetative storage proteins. Storage proteins of molecular weights in the range of 27-32 kD have been detected in increasing amounts in other species during the fall (Coleman et al. 1991, Ref. No. 7; Roberts et al. 1991, Ref. No. 52; Wetzel and Greenwood 1989, Ref. No. 67; Wetzel and Greenwood 1991, Ref. No. 68; Wetzel et al. 1989, Ref. No. 66). One of the storage proteins has been shown to consist of two basic forms and is rich in glutamine and asparagine (Wetzel and Greenwood 1991, Ref. No. 68).

Storage proteins are generally found in the bark. In contrast, the protein of interest in the present invention was isolated from foliage and, as noted above, consists of at least two acidic isoforms with identical N-terminal amino acid sequences. Although the size, charge and amino acid composition of this fall protein does not resemble those of vegetative storage proteins, the possibility of this protein being a storage protein could not initially be ruled out.

However, an observation that the cold protein present in late November samples of sugar pine accounted for approximately 5% of the total protein and was not detected in early October samples suggested a particular functional role for this protein. Since an increase in soluble proteins was found to be associated with frost hardiness in a *Pinus* species (Pomeroy and Siminovitch 1970, Ref. No. 50), the possibility that this cold protein might be involved in the development of cold hardiness existed. For this purpose, an antibody to the N-terminal peptide of the cold protein was raised by using a strategy which involved the synthesis of the N-terminal peptide and its coupling to a carrier protein. The conjugate was used as an immunogen to produce antibodies. The carrier protein was used because the size of the peptide itself is too small to be immunogenic. This strategy was successful since anti-peptide antibody was shown to bind specifically the cold protein. This result indicated that the antigenic epitope(s) of the protein was accessible to the anti-peptide antibody.

The seasonal variation in the concentration of this protein in sugar pine was confirmed with this antibody. One of the purposes of producing specific antibody to this cold protein was to examine for the presence of similar proteins in other conifers. Using this antibody, homologues of this cold protein were successfully detected in other conifers, specifically eastern and western white pine. The N-terminal sequence of the western white pine was found to be: Val—Ser—Gly—Thr—Ser—Ser—Thr—Glu—Glu—Val—Val—Gln—Val—Glu—Ala—Arg—Arg—Leu—Trp—Asn—Ala—Thr—Thr—Lys—Asp [SEQ ID NO:3].

Consistent with the antibody data, the N-terminal amino acid sequence (with the exception of amino acid position 13) was identical up to 20 amino acid residues.

Since western white pine is an important species for forest regeneration in British Columbia, a thorough study was undertaken to examine the seasonal variation of the cold protein in western white pine throughout the year. Results clearly indicate that the cold protein reaches its maximum content in the winter months, declines in the spring, and is below the detection level in the summer. There is no apparent variation in the appearance or disappearance of the cold protein in three seedlots used. Since the foliage from seedlings within these seedlots were pooled, the data did not provide any insight into variation within a seedlot. However, within seedlot variation was observed in experiment dealing with the association of cold protein with frost hardiness.

We have also examined the association of the cold protein with frost hardiness. Experiments on frost hardiness of western white pine seedlings clearly show a significant ($p<0.0001$) correlation ($R=0.797$) of the cold protein with frost hardiness and that frost hardiness (judged to be a resistance to damage in at least 50% of sample seedlings when exposed to temperatures of $-40°$ C.) is associated with protein levels of at least 0.33 ODxmm.

The same kind of assessment can be used to determine the minimum protein levels associated with frost hardiness of seedlings of other species, i.e. by finding levels associated with resistance to damage by at least 50% of the seedlings when exposed to temperatures of $-40°$ C.

While characterizing polypeptides encoded by cold regulated genes of *Arabidopsis thaliana*, Lin et al. (1990), Ref. No. 41, observed that a number of these polypeptides share the unusual property of remaining soluble in aqueous solution. We also examined this property in the cold proteins of the present invention. The hydrophathyplot of the amino acid sequence indicates that the N-terminal peptide is highly hydrophilic. This is also confirmed by high solubility of the synthetic N-terminal peptide. Moreover, the cold protein is also shown to be stable towards boiling.

In view of the above, it is clear that the 19 kD protein and its analogs are indicative of the frost-hardiness of the seedlings in which they are present. Consequently, the invention involves assessing the presence and amount of such proteins in foliage of seedlings to be investigated. Conifer foliage is rich in phenolic substances which may interfere with conventional electrophoretic separation of the proteins, but the use of sodium dodecyl sulfate (SDS) and mercaptoethanol as solvents for the protein overcomes this problem. The amount of cold protein in conifer tissues as determined with the antibody may be expressed per weight (e.g. mg) of the fresh tissue. However, to accurately compare the amount of cold protein in many samples, it is desirable to express the amount of the cold protein per weight of the extractable proteins present in the tissues. The present invention preferably relates to the extraction of protein with SDS and subsequent determination of proteins in the presence of SDS as described.

The antibody to the cold proteins can be made up into a test kit consisting, for example, of a supply of the antibody, a developing agent for indicating the presence of the antibody, a supply of the purified cold protein for use as a standard, equipment normally associated with antibody test kits (dipstick, blot or ELISA material) and suitable instructions.

The invention is further illustrated by the following Experimental Detail, which is provided only for the purpose of illustration and instruction.

EXPERIMENTAL DETAIL

MATERIALS AND METHODS
Sugar Pine (*Pinus lambertiana* Dougl.)

Seedlings [seedlot 39 from Mountain Home State Forest, Calif., U.S.A. (35° 14'N, 118° 40'W; elevation: 6000-3000 feet), and ZL from Bunker Hill, Calif., U.S.A. (39° 03'N; 120° 23'W; elevation: 6500-6900 feet)] were grown as described earlier (Hunt 1988, Ref. No. 35) for western white pine seedlings and kept under natural day length and temperature in a shade house at the Pacific Forestry Centre, Victoria, B.C., Canada (48° 25'N, 123°W; elevation: 100 feet). The seedlings were fertilized with N:P:K (20:20:20@0.5 g/L) twice a week and with FeSO$_4$(0.155 g/L) supplement once every two weeks (June 30 to October 31). On October 23 and October 31 the fertilizer used was N:P:K: (4:25:35@0.5 g/L). No fertilizer was used beyond October 31. The seedlings were watered twice a week during the entire experiment. The seedlings were 4 months old when first sampled. All foliage from each of four seedlings per seedlot was collected on October 5, October 11, October 20, November 15, and November 28.

Extraction of Proteins

Proteins were extracted as described elsewhere (Ekramoddoullah 1991, Ref. No. 14; 1993, Ref. No. 16) with minor modifications. Foliar samples were lyophilized and ground to powder in liquid nitrogen with a mortar and pestle after which 50 mg of needle powder was extracted with 0.7 mL of ES (4% SDS, 4% sucrose, 5% mercaptoethanol) for 10 minutes at room temperature with gentle stirring. The extract was centrifuged at 10,000 g, and the clear supernatant was heated at 100° C. for 3 min and then cooled at room temperature. Proteins were precipitated by adding cold (-20° C.) acetone (8X volume of the supernatant); precipitation was allowed to continue for 1 hour, after which the sample was centrifuged at 10,000 g. The pellet was resuspended in 0.2 mL of ES, centrifuged at 10,000 g, and the protein content of the supernate was determined (Ekramoddoullah 1992, Ref. No. 15; Ekramoddoullah and Davidson 1994, Ref. No. 18) using BSA as a standard. Briefly, the protein solution was spotted on a polyvinylidene difluoride membrane (IMMOBILON-P™, Millipore Canada Ltd., Toronto, Ontario). The membrane was stained with 0.1% Coomassie blue R-250 (Bio-Rad Laboratories, Richmond, CA) in 50% methanol for 8 min, and then destained in 50% methanol:10% acetic acid for 8 min at room temperature. The membrane was then rinsed with water for 10 min. The stained membrane was scanned by a laser scanner (Molecular Dynamics, model 110A, Sunnyvale, CA) interfaced with a workstation (SPARK™1, Sun Microsystems of Canada Inc., Vancouver, B.C.) and PDI (Protein+dna imageWare systems, Huntington Station, NY) for membrane blot processing with the software program ONED™. Scanning, detection and quantification were performed according to the PDI instruction manual.

1-Dimensional Gel Electrophoresis

SDS-PAGE was carried out in a protein slab cell apparatus (Bio-Rad) with 0.75 mm spacers utilizing a Laemmli buffer system (Laemmli 1970, Ref. No. 39). A sample volume of 10 µL (containing 5–30 µg protein) was applied in each well. To calibrate the gel, low-molecular-weight (range: 14.4–94 kD) standard markers (Pharmacia LKB, Montreal, Que) were used. The gel was stained with Coomassie blue, R-250 (Fairbanks et al. 1971, Ref. No. 21).

2-Dimensional Gel Electrophoresis

The 2-D gel electrophoresis of sugar pine proteins was performed following Hochstrasser et al. (1988), Ref. No. 30, with minor modifications (Ekramoddoullah 1990, Ref. No. 13). Gels were stained with silver (Hochstrasser et al. 1988, Ref. No. 30). To calibrate the gel, the following standard molecular weight and pI markers (Pharmacia LKB) were used: for the first dimension, carbamylated glyceraldehyde-3-phosphate dehydrogenases (34 isoforms in the pI range of 4.3–8.3 were used); for the second dimension, Pharmacia low-molecular-weight standard markers were used.

Scanning of Gels and Computer Analysis of Separated Proteins

Stained gels were scanned by a laser scanner (Molecular Dynamics) interfaced by PDI with ONED™ software for processing 1-D gel and blots and PDQUEST™ software (version 3.2) for processing 2-D gels. An original version of the software program was described by Garrels et al. (1984), Ref. No. 22. Briefly, 2-D gel scans obtained from gels were converted to gel images, which were then converted into gel spots by an auto-detection method. Scanning, detection, estimation of molecular weight and pI, and quantitiation of protein bands (1-D gels and Western immunoblots) or spots (2-D gels) were performed according to the PDI instruction manual.

Amino Acid Sequence and Composition Analyses

Pine proteins separated on ID or 2-D gels were electrophoretically transferred to IMMOBILON-P™ membrane as described by Matsudaira (1987), Ref. No. 44. For sequencing, the stained protein bands or spots were cut from the membrane and placed directly (Matsudaira 1987, Ref. No. 44) into the sequencer (Model 470A, Applied Biosystems, Foster City, CA) for N-terminal sequence analysis. For amino acid composition analysis, portions of membranes containing stained proteins were hydrolyzed in 6 N hydrochloric acid. Samples were purged with argon and the vials were sealed and heated in an over at 165° C. for 45 min. At the end of the hydrolysis, samples were dried under vacuum and processed in an automatic amino acid analyzer (Model 420, Applied Biosystems) according to the manufacturer's instruction manual. The amino acid analyses were performed at the University of Victoria Microsequencing Facility (Victoria, B.C. Canada).

The amino acid sequence comparison of the N-terminal peptide was performed at PIR (Protein Identification Resource Centre, Washington, D.C.) and at NCBI (National Centre for Biotechnology Information, Bethesda, MD) using FASTA (Pearson and Lipman 1988, Ref. No. 49) and BLAST (Altschul et al. 1990, Ref. No. 1) network services.

The hydrophilicity of the N-terminal peptide was determined at Multiple Peptide System(MPS) (3550 General Atomics Court, San Diego, CA 92121) using the SMP-SAID™ program based on the hydrophilicity scale of Houghton and Ostresh (1987), Ref. No. 34.

Synthesis of N-terminal Peptide and Production of Rabbit Anti-peptide Polyclonal Antibodies The following peptide:
Val—Ser—Gly—Thr—Ser—Ser—Thr—Glu—Glu—Val—Val—Gln—Asn—Glu—Ala—Arg—Arg—Cys [SEQ ID NO:2]
was synthesized using a variation of Merrifield's original solid phase procedures (Merrifield, 1963, Ref. No. 45) in conjunction with the method of simultaneous peptide synthesis (SMPS) (Houghton, 1985, Ref. No. 33). The first seventeen amino acids were a part of the N-terminal amino acid sequence of the protein Pin 1 I [SEQ ID NO:1] and the eighteenth amino acid, i.e. cysteine, was added at the C-terminal end of the peptide to facilitate the coupling of the peptide to a carrier protein.

Conjugation: 5 mg of purified peptide were coupled through the terminal cysteine thiol to a carrier protein, keyhole limpet haemocyanin (KLH), with the heterobifunctional cross-linking agent, Maleimidobenoyl-N-hydroxysuccinimide ester (MBS), in a ratio of 1 part peptide to 1 part keyhole limpet haemocyanin (KLH) (w/w).

Immunization of rabbits: The peptide was suspended in PBS buffer (3.1 mg/mL), emulsified by mixing with an equal volume of Greund's adjuvant, and injected into five to six subcutaneous dorsal sites, for a total volume of 0.6 mL (1.0 mg of conjugate, 0.50 mg peptide) per immunization. Rabbits were repeatedly (over 60 days) injected with the immunogen under a proprietary immunization schedule.

Affinity purification of antibody: Immunoaffinity gel and antibody purification were carried out with an affinity purification kit PROTON™ Kit #1 (MPS). Ten mg of the synthetic peptide were coupled to 2 mL of activated agarose gel. After deactivation of the remaining activated sites, the gel was equilibrated in a physiological buffer at pH 7.5 at room temperature. Five mL of crude antisera were applied to gel containing column. After washes, the adsorbed protein was eluted with sodium phosphate buffer at low pH and collected in HEPES [4(2-Hydroxyethyl)-1-piperazineethanesulfonic acid] buffer designed to neutralize the elution buffer. The purity of the anti-peptide antibody was checked by SDS-PAGE.

Western Immunoblot

Proteins separated by SDS-PAGE were electrophoretically transferred (Towbin et al. 1979, Ref. No. 61) from the gel onto IMMOBILON-O™ membrane. Following transfer of the separated proteins, the membrane was blocked by incubating it in gelatin [3% in Tris-buffered saline (TBS), 20 mM Tris-HCl, 500 mM NaCl, pH 7.5] for 30 min at room temperature and was then washed with TBST (TBS containing 1% TWEEN™ 20). The membrane was incubated with rabbit anti-peptide antibody diluted 500 fold with incubation buffer (IB) 1% gelatin in TBS) overnight at room temperature. The membrane was washed with TBS for 5 min, with the washing repeated three times, and then incubated with the conjugate of goat anti-rabbit IgG (H+L) and alkaline phosphatase (Bio-Rad) diluted 2000-fold with IB for 1 hour. The membrane was again washed with TBS as above. The alkaline phosphatase color development reagents (Bio-Rad, immunoblot assay kit) BCIP (5-bromo, 4-chloro 3-idolyphosphate p-toluidine salt) and NBT (p-nitro blue tetrazolium chloride) were used to develop the color reaction. To calibrate the Western blot, rainbow coloured protein molecular markers (range: 14.3–200 kD) (Amersham International plc, Amersham Place, England) were used. The blot was scanned and processed using software program ONED™.

Western White Pine (*Pinus monticola* D. Don)

Seasonal variation of the cold protein: Western white pine seedlings from seedlots 3159 [Ingersoll Creek (50° 008' N, 118° 4.8'W; elevation 2600 feet), British Columbia, Canada]; 2881 [Eagle River (50° 57.5'N, 118° 45'W; elevation 1200 feet), British Columbia, Canada]; and 2888 [Angus Creek (49° 32'N, 123° 44'W; elevation 650 feet), British Columbia Canada] were grown (Hunt 1988, Ref. No. 35) and kept under natural day length and temperature in a shade house at the Pacific Forestry Centre. They were fertilized with N:P:K (20:20:20@0.5 g/L) weekly (July 1 to Aug 29), with N:P:K (15-30-15@0.5 g/L) weekly (August 30 to October 1), and with N:P:K (8-20-30@0.5 g/L) weekly (Oct 2 to October 26). No fertilizer was used between Oct 27 and March 25 of the next year. Seedlings were watered twice a week during the entire experiment. From March 25 to Aug 30 of the next year, seedlings were again fertilized weekly with N:P:K (20:20:20@0.5 g/L). Seedlings were four months old when first sampled. One needle from each seedling was collected monthly for a year (August to July). Needles were pooled per seedlot (36 seedlings/ seedlot) for a given date. To quantify the cold-protein, foliage proteins were extracted, separated by SDS-PAGE, and then by Western-immunoblot using rabbit anti-peptide antibodies.

Assessment of frost hardiness and the level of cold protein: Ninety-two two-year old western white pine seedlings [seedlot 2368, Mt Hooke (49° 04'N, 124° 12'W; elevation: 235 feet) British Columbia, Canada] were raised outdoors at the University of Victoria (48° 25'N, 123°W; elevation: 100 feet) for one growing season. Seedlings were watered weekly, and were fertilized with N:P:K (20:4:20@0.5 g/L) every two weeks. Foliage of individual trees was harvested five times between November and July. Ten needles per tree were kept aside for the quantification of the cold protein and twenty needles were used for frost hardiness assessment. The needles were cut into 5 mm sections. For each seedling, ten needles sections, plus 2 mL distilled water, were placed into each of 12, 15 mL scintillation vials. Three scintillation vials were kept as unfrozen controls. Freezing was carried out in a programmable chest freezer (Caltec Scientific Ltd., Richmond, B.C.), which was set to cool from 0° C. at a rate of 5° C./h to −11° C. This temperature was held for 1 hour, and then the first replicate of 3 samples per tree was removed. Cooling continued at the same rate of −16° C. and then −21° C. At each of these temperatures, conditions were again held steady for 1 hour, then a replicate of 3 samples was removed. Freezer temperature and the temperature of the liquid inside several vials were monitored. After freezing, the vials were removed to a refrigerator and kept at 4° C. for 18 hours. Then mL of distilled water was then added to each vial, and after a 2 hour interval, conductivity measurements of electrolyte leakage from the foliage were made. All vials were then heated to 100° C. in an oven for 2 hours, cooled for 18 hours, and conductivity was remeasured. The index of injury was calculated from the conductivity measurements using the formulae of Colombo et al.(1984), Ref. No. 10. The temperature resulting in 50% damage to samples was interpolated from the index of injury results at the three freezing temperatures. To examine the correlation between the frost hardiness and the level of cold protein, a linear regression analysis (SAS Institute Inc. 1988, Ref. No. 55) for these two variables was performed.

To determine the content of the cold protein, proteins were extracted from the needles of same trees (i.e. whose needles were subjected to frost hardiness) harvested five times between November and July. Proteins were separated by SDS-PAGE, followed by Wester-immunoblot using rabbit anti-peptide antibodies. One of the samples containing a sufficient amount of this cold protein (as determined in a preliminary experiment by Western-immunoblot) was used as a reference standard to quantify the cold protein in all samples involving several Western-immunoblots. The level of cold protein was normalized with respect to this reference standard.

Eastern White Pine

The presence of cold protein in another five-needle pine, eastern white pine (*Pinus strobus* L.) was examined by Western-immunoblot. For this purpose, foliage (bulk sample) of ten eastern white pine mature trees was collected in February, 1994 from Quebec City, Quebec, Canada.

RESULTS

Sugar Pine

Figure 2:
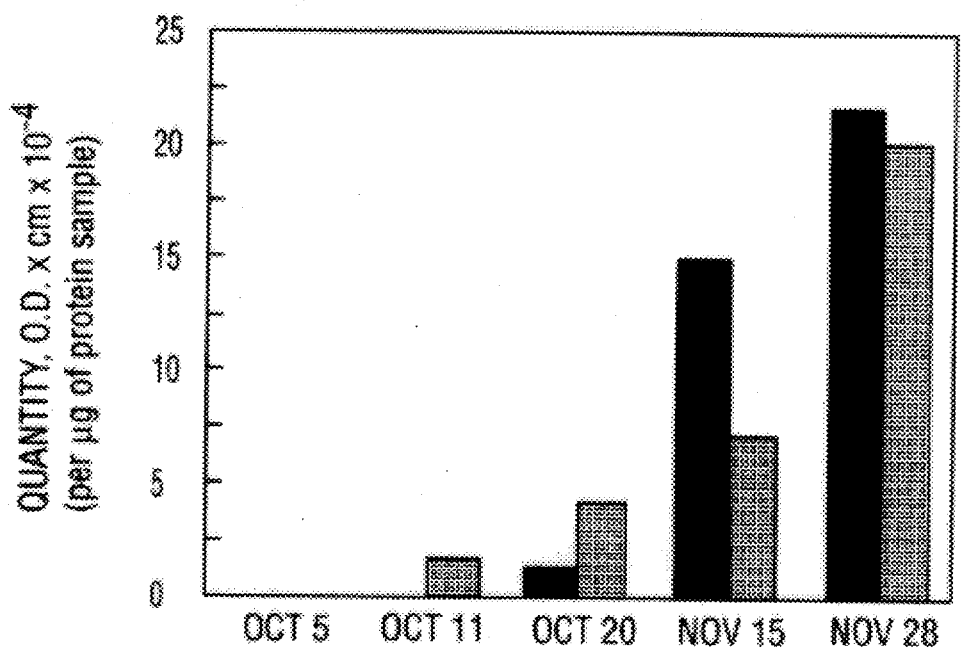
FIG. 2 shows the accumulation of the 19 kD protein of sugar pine in the fall as explained in the Experimental Detail below. The solid bar indicates seedlings of seedlot 39; the spotted bar indicates seedlings of seedlot ZL. The quantity of the 19 kD band in each sample was normalized with respect to the amount of proteins loaded onto 1-dimensional SDS-PAGE gels.

Detection of a protein in sugar pine in increasing amounts in the fall: A 19 kD protein was first detected in samples collected from one seedlot on October 11 (FIG. 1, indicated by the arrow), and was present in seedlings of both seedlots on October 20; this protein increased in quantity until November 28 (FIG. 2). The relative percentage of this protein band (i.e. relative to all protein bands) present in the November 28 samples was 5.4 and 4.6 for seedlings of seedlot 39 and ZL, respectively. In samples taken the following summer, this protein could not be detected (data not shown).

Characterization and N-terminal amino acid sequence of Pin 1 I: The 19 kD protein was tentatively designated as Pin 1 I (Pin for *Pinus*, 1 for lambertiana and I for the first protein of sugar pine to be characterized). Samples from seedlings (seedlot 39) collected on October 5 and November 28 were again subjected to one-dimensional gel electrophoresis and electro-blotted onto membranes for amino acid composition and sequence analyses. Both the sample collected on October 5 and standard molecular markers served as references for the easy identification of the 19 kD component on the blot which allowed subsequent cutting of the band. The amino acid composition of Pin 1 I (shown in Table 1 below) revealed no predominance of a particular amino acid.

TABLE 1

Amino acid composition of Pin 1 I

| Amino acid | Residues/molecule |
|---|---|
| Asx | 15 |
| Glx | 19 |
| Ser | 10 |
| Gly | 16 |
| His | 2 |
| Arg | 8 |
| Thr | 8 |
| Ala | 14 |
| Pro | 7 |
| Tyr | 4 |
| Val | 13 |
| Met | 1 |
| Cys | 0 |
| Ile | 7 |
| Leu | 16 |
| Phe | 7 |
| Lys | 16 |

The N-terminal amino acid sequence of this protein is shown below:
Val—Ser—Gly—Thr—Ser—Ser—Thr—Glu—Glu—Val—Val—Gln—Asn—Glu—Ala—Arg—Arg—Leu—Trp—Asn [SEQ ID NO:1]

The hydropathy plot derived from the amino acid sequence indicated that the N-terminal peptide was hydrophilic and indeed the synthetic N-terminal peptide was found to be highly water soluble. A similarity search revealed that the peptide had 42.1% identity with gp-alpha and DNA primase with a 19 amino acid overlap and varying sequence identity was observed with several proteins with an overlap of fewer amino acids.

Figure 3:
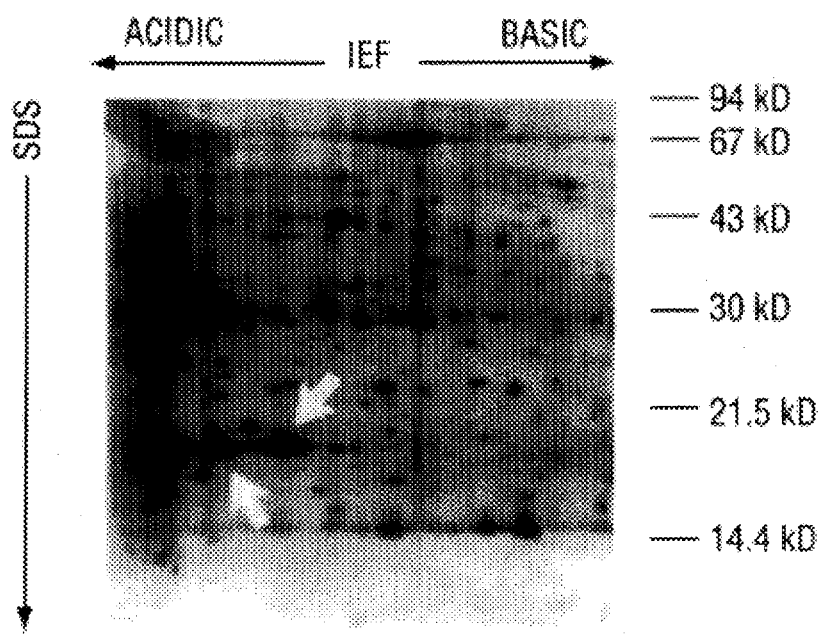
FIG. 3 shows a two-dimensional gel electrophoresis of sugar pine foliar protein sample of seedlings of seedlot 39 collected on November 28 as explained in the Experimental Detail below. The left side of the gel is the acidic end and the right side is the basic end. Positions of standard molecular weight markers are indicated on the right side. Two acidic isoforms (pI 5.9 and 6.2) of Pin l I are indicated by arrows. These two protein spots were absent on the 2-D gel electrophorogram (not shown) of samples collected on October 5 of the same year.

The two samples were also subjected to two-dimensional gel electrophoresis. Only the November 28 sample is shown (FIG. 3). Although several proteins were different between the two samples (October 5 and November 28), the two major proteins (indicated by the arrows) were detected in the acidic and 19 kD region of November 28 samples and were absent in the October 5 samples. The pI's of the two isoforms were 5.9 and 6.2. The relative percentage (i.e. of the resolved proteins) of the isoform with a pI value of 5.9 was 2 and that of the other isoform (pI 6.2) was 6. Another set of two-dimensional gels were blotted for amino acid sequence analysis. The N-terminal amino acid sequences of these two proteins and Pin 1 I were found to be identical.

Figure 4:
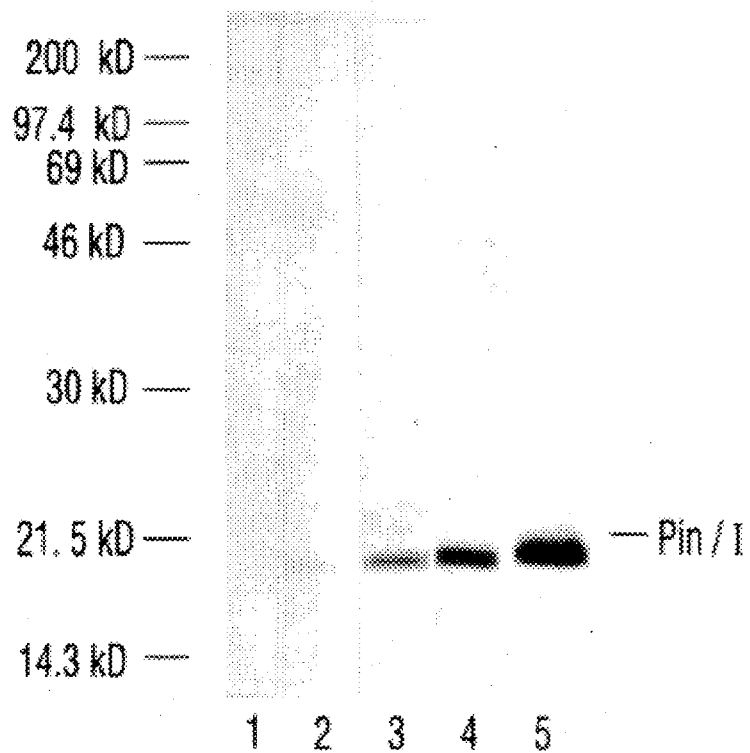
FIG. 4 shows the specificity of anti-peptide antibody as demonstrated by Western-immunoblot as explained in the Experimental Detail below. Proteins (10 μg/lane) of sugar pine foliage samples (seedlot ZL) were separated by SDS-PAGE followed by Western blot. The blot was detected with rabbit anti-peptide antibody. Lanes 1–5 are samples collected on October 5, October 11, October 20, November 15, and November 28, of the same year, respectively. Positions of standard (rainbow) molecular weight markers are indicated on the left side and the position of the Pin l I band is shown on the right.
Figure 5:
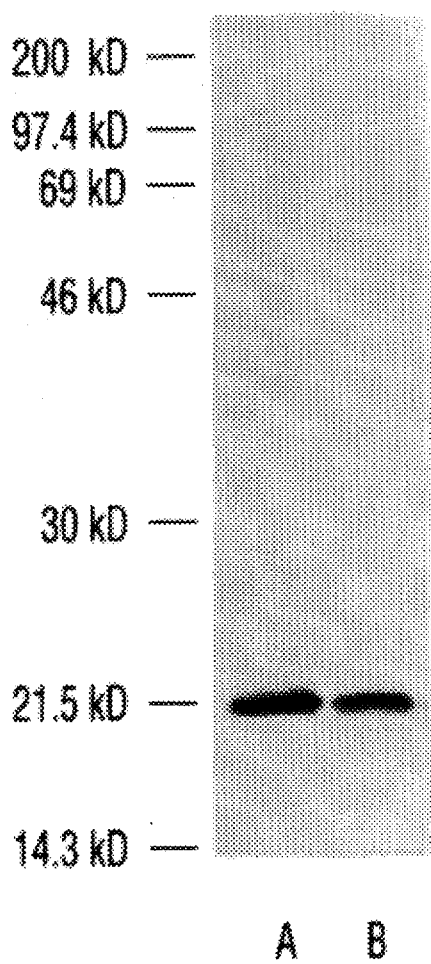
FIG. 5 shows the detection of homologues of Pin l I in western and eastern white pine by Western-immunoblot as explained in the Experimental Detail below. Proteins (5 μg/lane) of western (lane A) and eastern white pine (lane B) were separated by SDS-PAGE followed by Western blot. The blot was detected with rabbit anti-peptide antibody. Positions of standard (rainbow) molecular weight markers are indicated on the left side.

Specificity of rabbit polyclonal anti-peptide antibodies: Western-immunoblot data (FIG. 4) showed that the antipeptide antibodies specifically bound to a single major protein band of sugar pine corresponding to 19 kD and the intensity of the band was more in samples collected at a later date. Western White Pine Detection of the homologous protein in western and eastern white pine: Having demonstrated the specificity of anti-peptide antibody, the antibody was used in a Western-immunoblot to detect the homologous proteins in eastern and western white pine corresponding to similar size (FIG. 5). The homologous protein in western white pine was designated as Pin m III, while Pin m I and Pin m II were two previously designated proteins in western white pine (Ekramoddoullah 1993, Ref. No. 17). An acetone pellet of crude protein extracts of western white pine foliage containing the cold-protein was boiled in water for 5 min. After centrifiguation, the aqueous solution, as tested by immunoblot, contained Pin m III demonstrating that this protein was stable towards boiling.

Figure 6:
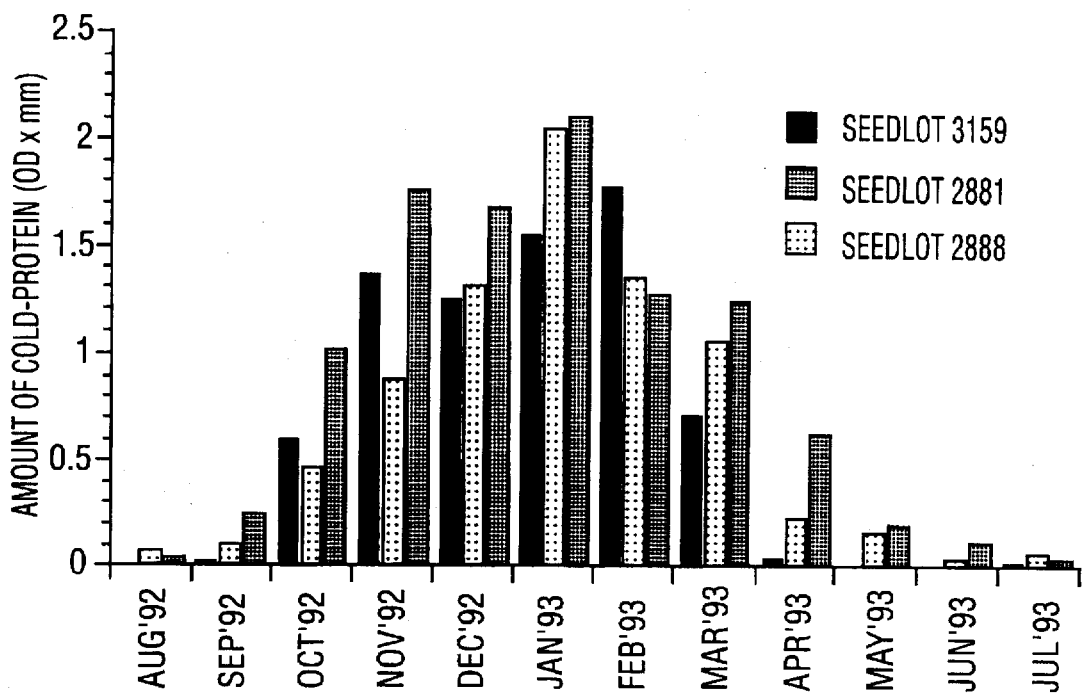
FIG. 6 shows the association of Pin m III with overwintering of western white pine seedlings as explained in the Experimental Detail below. Four-months old seedlings were kept in shelter house under natural daylength and temperature. The foliage was collected monthly. For each collection date, a single needle per tree was pooled from 36 trees within a seedlot. The cold-protein was quantified by Western-immunoblot using rabbit antipeptide antibody.
Figure 8:
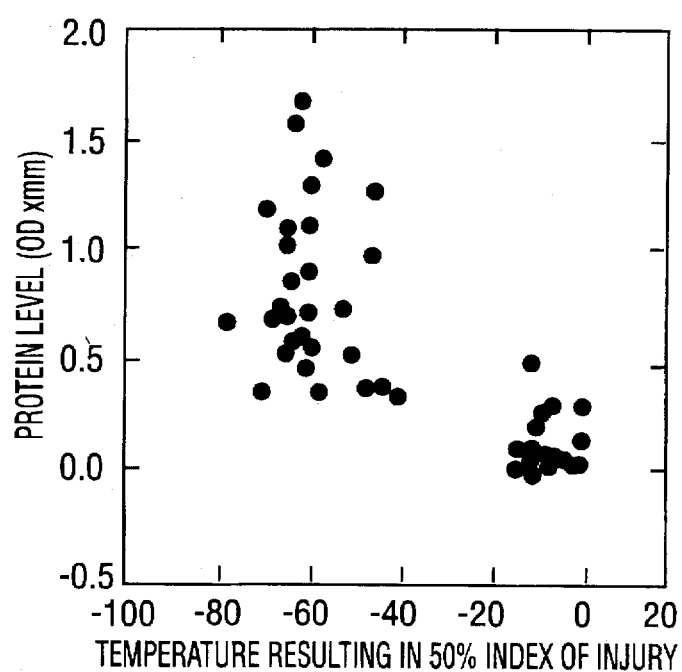
FIG. 8 shows the association of the cold protein with frost hardiness of two-year old western white pine seedlings as explained in the Experimental Detail below. A linear regression analysis of frost hardiness and protein level of ninety western white pine seedlings. The correlation (R=0.797) of these two variables was highly significant (p<0.0001).

An association of the Pin m III with overwintering and frost hardiness of western white pine seedlings: The data shown in FIG. 6 illustrate the seasonal variation of the cold-protein in four months-old (when first sampled) western white pine seedlings. Cold-protein content increased as fall progressed, reached a maximum in winter months, and decreased to low levels in summer months. These results indicate that this cold protein is associated with overwintering of pine seedlings. FIG. 7 shows the level of the cold protein and the corresponding frost hardiness of 2-year old white pine seedlings as they overwintered. The level of the cold protein and the frost hardiness of these trees were at a maximum in January. A plot (FIG. 8) of regression analysis of the protein level and temperature resulting in 50% index of injury of individual trees shows that there is a significant correlation ($R=0.797$, $p<0.0001$) between these two variables. The regression plot also shows that there are two main groupings of data points with a fair amount of scatter in the most frost hardy trees. From these results it may be concluded that a protein level greater than 0.33 indicates a frost hardy tree (LT50<−40° C.). For the sake of brevity, proteins Pin 1 I and Pin m III will also be termed Cold Proteins (cold to reflect the fact that the protein was induced more in colder months) to represent a family of proteins in conifers which may have a common physiological function.

The N-terminal amino acid sequence of Pin m III is shown below:
Val—Ser—Gly—Thr—Ser—Ser—Thr—Glu—Glu—Val—Val—Gln—Val—Glu—Ala—Arg—Arg—Leu—Trp—Asn—Ala—Thr—Thr—Lys—Asp [SEQ ID NO:3].

The sequence shows 100% (except amino acid position 13) identity up to first 20 amino acid residues. An additional 5 amino acid residues (i.e. up to position 25) was clearly obtained for Pin m III.

REFERENCES

1. Altschul SF, Gish W, Miller W, Meyers EW, Lipman DJ 1990) Basic logical alignment search tool. J. Mol. Biol. 215:403–410

2. Anderson JV, Chevone, BI, Hess, JL (1992) Seasonal variation in the antioxidant system of eastern white pine needles: evidence for thermal dependence. Plant Physiol. 98:501–508

3. Asada K, Takahasi M (1987) Production and scavanging of active oxygen in photosynthesis. In DJ Ky, CB Osmond, CD Arntzen, eds, Topics in photosynthesis. "Photoinhibition" vol 9, Elsevier, Amsterdam, pp 227–287

4. Vewley JD, Oliver MJ (1992) Dessication tolerance in vegetative plant tissues and seeds: protein synthesis in relation to dessication and a potential role for protection and repair mechanism. In GN Somero, CB Osmond, CL Bolis, eds, Water and Life. Springer, Berlin, pp 141–160

5. Binh LT, Oono K (1992) Molecular cloning and characterization of genes related to chilling tolerance in rice. Plant Physiol. 99:1146–1150

6. Close TJ, Lortt AA, Chandler PM (1989) A cDNA-based comparison of dehydration-induced proteins (dehydrins) in barley and corn. Plant Mol Biol 13:95–108

7. Coleman GD, Chen TH, Ernst SG, Fuchigami L (1991) Photoperiod control of poplar bark storage protein accumulation. Plant Physiol. 96:686–692

8. Coleman GD, Chen TH, Ernst SG, Fuchigami L (1992) Complementary DNA cloning of poplar bark storage protein and control of the expression by photoperiod. Plant Physiol. 98:687–693

9. Coleman GD, Chen TH (1993) Sequence of poplar bark storage protein gene. Plant Physiol. 102:1347–1348

10. Colombo SJ, Webb DP, Glerum C (1984) Frost hardiness testing: an operational manual for use with extended greenhouse culture. Ontario Ministry of Natural resource, Maple For. Res. Rep. 110.

11. de Kok LJ, Oosterhuis FA (1983) Effects of frost-harding and salinity and sulfhydryl levels and on glutathione reductase activity in spinach leaves. Physiol Plant 58:47–51

12. Dunman JG, Xu L, Neven LG, Tursman D, Wu DW (1991) Hemolymph proteins involved in insect subzero temperature tolerance: ice nucleators and antifreeze proteins. In Insects at Low Temperature, eds. R. E. Lee, Jr., D. L. Denlinger, pp. 94–127. New York: Chapman and Hall.

13. Ekramoddoullah AKM (1990) Two-dimensional gel electrophoretic analyses of Kentucky bluegrass and rye grass pollen allergens: Detection with a murine monoclonal anti-Poa p I antibody and amino terminal amino acid sequence of Poa p I allergen. Int Arch Allergy Appl Immunol 93:371–377.

14. Ekramoddoullah AKM (1991) Analysis of proteins of western white pine (*Pinus moticola* Dougl.) needles. In Rusts of Pine. Proc. 3rd IUFRO Rusts of Pine Working Party Conference, Sept. 18–22, 1989, Banff, Alberta. Edited by Y. Hiratsuka, J. K. Samoil, P. V. Blenis, P. E. Crane, and B. L. Laishely. For Can, Northwest Reg., North. For Cent., Edmonton, Alberta. Inf. Rep. Nor-X-317. pp. 102–108

15. Ekramoddoullah AKM (1992) An innovative approach to determination of nanogram quantities of protein whereby the interference by sodium dodecyl sulfate (SDS) and mercaptoethanol was eliminated. FASEB J. 6: NO 4 and 5, 1992.

16. Ekramoddoullah AKM (1993) Analysis of needle proteins and N-terminal amino acid sequence of two photosystem II proteins of western white pine (*Pinus monticola* D. Don). Tree Physiology 12:101–106

17. Ekramoddoullah AKM, Hunt RS (1993) Changes in protein profile of susceptible and resistant sugar pine foliage infected with white pine blister rust fungus, *Cronartium ribicola*. Can. J. Plant Pathol. 15:259–264.

18. Ekramoddoullah AKM, Davidson JJ (1994) A method for the determination of conifer foliage protein extracted using sodium dodecyl sulfate and mercaptoethanol. Phytochemical Analysis. in press.

19. Esterbauer H, Grill D (1978) Seasonal variation of gluthathione and glutathione reductase in needles of *Picea abies*. Plant Physiol 61:119–121

20. Esterbauer H, Grill D, Welt R (1980) Der jahreszeitliche rhythmus des ascorben-sauresystems in nadien von *Picea abies*. Z Pflanzephysiol 98:393–402

21. Fairbanks G, Steck TL, Wallach DFH (1971) Electrophoretic analysis of the major polypeptides of human erythrocyte membrane. Biochemistry 10:2606–2616.

22. Garrels JI, Farrar JT, Burwell IV CB (1984) The QUEST system for computer-analyzed two-dimensional electrophoresis of proteins. Pages 37–91 in J. E. Celis, and R. Bravo, editors. Two-dimensional gel electrophoresis of proteins (Methods and applications). Academic Press, New York. 487p 23. Gusta LV, Wesser CJ (1972) Nucleic acid and protein changes in relation to cold acclimation and freezing injury of Korean boxwood leaves. Plant Physiol. 49:91–96

24. Guy CL, Carter JV (1984) Characterization of partially purified gluthathione reductase from cold-hardened and non-hardened spinach leaf tissue. Cryobiology 21:454–464

25. Gu CL (1990) Cold acclimation and freezing stress tolerance: role of protein metabolism. Annu. Rev. Plant Physiol. Plant Mol. Biol. 40:187–223.

26. Hanson AD (1992) Compatible solute synthesis and compartmentation in higher plants. In GN Somero, CB Osmond, CL Bolis, eds, Water and Life. Springer, Berlin, pp 52–60

27. Hincha DK, Heber U, Schmitt JM (1989) Freezing ruptures thylakoid membranes in leaves, and rupture can be prevented in vitro by cryoprotective proteins. Plant Physiol Biochem 27:795–801.

28. Hincha DK, Hever U, Schmitt JM (1990) Proteins from frost-hardy leaves protect thylakoids against mechanical freeze-thaw damage in vitro. Planta 180:416–419.

29. Hincha DK, Bakaltcheva, I, Schmitt, JM (1993) Galactosespecific lectins protect isolated thylakoids against freeze-thaw damage. Plant Physiol. 103:59–65.

30. Hochstrasser DF, Harrington MG, Hochstrasser A-C, Miller MJ, Merril CR (1988) Methods for increasing the resolution of two-dimensional protein electrophoresis. Anal. Biochem. 173:424–435

31. Hofener R, Vazquez-Moreno L, Winter K, Bohnert JH, Scmitt JM (1987) Induction of crassulacean acid metabolism in *Mesembryanthemum crystallium* by high salinity: mass increase and de nov synthesis of PEP-Carboxylase. Plant Physiol 83:915–919

32. Houde M, Danyluk J, Laliberte JF, Rassart E, Dhindas RS, Sarhan F (1992) Cloning, characterization, and expression of a carrier DNA encoding a 50-kilodalton protein specially induced by cold acclimation in wheat. Plant Physiol. 99:1381–1387

33. Houghten RA (1985) General method for the rapid solid-phase synthesis of large number of peptides: Specificity of antigen-antibody interaction at the level of individual amino acids. Proc. Natl. Acad. Sci. USA 82:5131–5135

34. Houghton RA, Ostresh JM (1987) Confromational Influences upon peptide retention behavior in reverse phase high performance liquid chromatography. Biochromatography 2:80–84.

35. Hunt RS (1988) White pine tree improvements in British Columbia. In Proceedings of a western white pine management symposium, Nakusp, British Columbia, May 2–5, 1988, Forestry Canada, Pacific Forestry Centre, Victoria, B.C. Compiled by R. S. Hunt pp 32–36

36. Johnson-Flanagen AK, Sink J. (1987) Alteration of gene expression during the induction of freezing tolerance in *Brassica napus* suspension cultrues. Plant Physiol. 85:699–705

37. Kang SM, Titus JS (1980) Qualitative and quantitative changes in nitrogeneous compounds in senescing leaf and bark tissues of the apple. Physiol. Plant. 50:285–290

38. Kurkela S, Franck M (1990) Clining and characterization of a cold- and ABA-inducible *Arabidopis* gene. Plant Mol Biol 15:137–144

39. Laemmli UK (1970) Cleavage of structural proteins during the assembly of the head of bacteriophage T4. Nature. 227:680–685

40. Lavender DP (1985) Bud dormancy. In Proceedings: Evaluating seedling quality: principles, procedures, and predictive abilities of major tests. Workship held Oct. 16–18, 1984. Edited by M. L. Duryea. Forest Research Laboratory, Oregon State University, Corvallis. ISBN 0-87437-000-0. pp. 7–15

41. Lin C, Guo WW, Everson W, Thomashow MF (1990) Cold acclimation in Arabiodpsis and wheat—a response associated with expression of related genes encoding boiling-stable polypeptides. Plant Physiol. 94:1078–1083

42. Lin C, Thomashow MF (1992) DNA sequence analysis of a complementary DNA for cold-regulated Arabiodopsis gene COR-15 and characterization of the COR-15 polypeptide. Plant Physiol 99:519–525

43. Marentes E, Griffith M, Mlynarz A, Brush RA (1993) Proteins accumulate in the apoplast of winter rye leaves during cold acclimation. Physiollgia Plantarum 87:499–507

44. Matsudaira P (1987) Sequence from picomole quantities of proteins electroblotted onto polyvinylidene difluoride membranes. J. Biol. Chem. 262:10035–10038

45. Merrifield RB (1963) Solid phase peptide synthesis. I. The synthesis of a tetrapeptide. J. Amer. Chem. Soc. 85:2149–2154

46. Mohapatra SS, Wolfrain L, Poole RJ, Rhindsa RS (1989) Molecular cloning and relationship to freezing tolerance of cold-acclimated-specific genes of alfalfa. Plant Physiol. 89:375–380

47. Nakagawara S, Sagisaka S (1984) Increases in enzyme activities related to ascorbate metabolism during cold acclimation in poplar twigs. Plant Cell Physiol 25:899–906

48. Neven LG, Haskell DW, Guy, CL, Denslow N, Kelin PA, Green LG, Silverman A (1992) Association of 70-kilodalton heat-shock cognate proteins with acclimation to cold. Plant Physiol. 99:1362–1369

49. Pearson WR, Lipman DJ (1988) Improved tools for biological sequence comparison. PNAS 85:2444–2448.

50. Pomeroy MK, Siminovitch D (1970) Seasonal biochemical changes in the living bark and needles of red pine (*Pinus resinosa*) in relation to adaptation to freezing. Can. J. Bot. 48:953–967

51. Robberecht R, Junttila O (1992) The freezing response of an arctic cushion plant, *Saxifrage caespiotosa* L-acclimation, freezing tolerance and ice nucleation. Annals of Botany 70:129–135

52. Roberts DR, Toivonen P, McInnis SM (1991) Discrete proteins associated with overwintering of interior spruce and Douglas-fir seedlings. Can. J. Bot. 69:437–441.

53. Saez-Vasquez JS, Raynal M, Meza-Basso L, Delseny M. (1993) Two related, low-temperature-induced genes from *Brassica napus* are homologous to the human tumour bbcl (breast basic conserved) gene. Plant Mol Biol 23:1211–1221

54. Sagisaka S (1985) Injuries of cold acclimated poplar twigs resulting from enzyme inactivation and substrate depression during frozen storage at ambient temperatures for a long period. Plant Cell Physiol 26:1135–1145

55. SAD Institute Inc (1988) SAD/STAT™ User's Guide, Release 6.03 Edition. SAD Institute Inc. Carey, N.C.

56. Sauter JJ, Cleve VB (1993) Occurrence of maltose pool and maltase in poplar wood (*Populus* x *canadensis* <robusta>) during fall. J. Plant Physiol. 141:248–250

57. Schoner S, Foyer C, Lelandais M, Krouse GH (1989) Increase in activities of scavengers for active oxygen in spinach related to cold acclimation in excess light: VIII. International Congress on Photosynthesis, Stockholm. Physiol Plant 76:A99

58. Storey KB, Storey JM (1988) Freeze tolerance in animals. Physiol. Rev. 68:27–84

59. Thomas BR, Lester DT (1992) An examination of regional, provenance, and family variation in cold hardiness of *Pimus monticola*. Can. J. For. Res. 22:1917–1921

60. Thomashow MF, Gilmour SJ, Hajela R, Horvath D, Lin C, Guo W (1990) Studies on cold acclimation in *Arabidopsis thaliana*. Hortic. Biotechnol. 11:305–314

61. Towbin H, Stachelin T, Gordon J (1979) Electrophoretic transfer of proteins from polyacrylamide gels to nitrocellulose sheets: procedure and some applications. Proc. Natl. Acad. Sci. USA 76:4350–4354

62. Vierling RA, Nguyen HT (1992) Heat-shock proteins gene expression in diploid wheat genotypes differing in thermal tolerance. Crop Science. 32:4350–4354

63. Voinkov VK, Korytov MV (1991) Synthesis of stress proteins in winter wheat seedlings during hardening to cold. Soviet Plant Physiology (English translation). 38:696–960

64. Weiser CJ (1970) Cold resistance and injury in woody plants. Science 169:1269–1278

65. Weiser RL, Wallner SJ, Waddell JW (1990) Cell wall and extensin mRNA changes during cold acclimation of pea seedlings. Plant Physiol. 93:1021–1026

66. Wetzel S, Demmers C, Greenwood JS (1989) Seasonally fluctuating bark proteins are a potential form of nitrogen storage in three temperate hardwoods. Planta 178:275–281

67. Wetzel S, Greenwood JS (1989) Proteins as a potential storage compound in bark and leaves of several softwoods. Trees 3:149–153

68. Wetzel S, Greenwood JS (1991) The 32-kilodalton vegetative storage protein of *Salix microstachya* Turz: Characterization and Immunolocalization. Plant Physiol. 97:771–777

69. Zhu B, Chem THH, Li PH (1993) Expression of an ABA-responsive osmotin-like gene during the induction of freezing tolerance in *Solanum commersonni*. Plant Mol Biol 21:729–735

The disclosures of the above publications are incorporated herein by reference.

I claim:

1. A method of determining frost hardiness of a conifer seedling, which comprises detecting an amount of a cold protein in tissue of said seedling, said cold protein being a protein of approximately 19 kD that increase significantly in amount in said conifer during fall season (autumnal) months and that is associated with seedlings having frost hardiness, and assessing frost hardiness based on said detected amount.

2. A method according to claim 1 wherein said protein is a protein that binds to an antibody raised against a protein conjugate incorporating a peptide sequence as follows:

Val—Ser—Gly—Thr—Ser—Ser—Thr—Glu—Glu—Val—Val—Gln—Asn—Glu—Ala—Arg—Arg—Cys [SEQ ID NO:2].

3. A method according to claim 1 wherein said seedling is a seedling of the species *Pinus*, and said cold protein includes the N-terminal amino acid sequence:

Val—Ser—Gly—Thr—Ser—Ser—Thr—Glu—Glu—Val—Val—Gln—Asn—Glu—Ala—Arg—Arg—Leu—Trp—Asn [SEQ ID NO:1] or an homologue thereof.

4. A method according to claim 1 wherein said seedling is a seedling of *Pinus lambertiana* and said cold protein includes the N-terminal amino acid sequence: Val—Ser—Gly—Thr—Ser—Ser—Thr—Glu—Glu—Val—Val—Gln—Asn—Glu—Ala—Arg—Arg—Leu—Trp—Asn [SEQ ID NO:1].

5. A method according to claim 1 wherein said seedling is a seedling of *Pinus monticola* and said cold protein includes the amino acid sequence: Val —Ser—Gly—Thr—Ser—Ser—Thr—Glu—Glu—Val —Val—Gln—Val —Glu—Ala—Arg—Arg—Leu—Trp —Asn—Ala—Thr—Thr—Lys—Asp [SEQ ID NO:3].

6. A method according to claim 1 wherein a level of said protein associated with frost hardy seedlings is first determined by measuring protein levels of a plurality of seedlings, exposing said seedlings to low temperatures and plotting protein levels of said seedlings against temperatures resulting in a 50% index of injury to individual seedlings, and then determining a minimum protein level associated with frost hardy seedlings having less than 50% injury when exposed to –40° C., and using said minimum protein level to determine frost hardiness of other seedlings of the same species.

7. A method according to claim 1 wherein said protein is detected by exposing seedling tissue to an antibody that binds to said protein, removing excess antibody and detecting for antibody bound to said seedling tissue.

8. An antibody that binds to a cold protein of approximately 19 kD that increases significantly in amount in conifer seedlings during fall season (autumnal) months and that is associated with seedlings having frost hardiness.

9. A method of planting conifer in a region subject to freezing temperatures for improved resistance to damage by frost, comprising producing seedlings of said conifer, determining frost hardiness of said seedlings, eliminating seedlings determined not to be suitably frost hardy, and planting the remaining frost hardy seedlings in said region, wherein said frost hardiness of said seedlings is determined by detecting an amount of a cold protein in tissue of said seedling, said cold protein being a protein of approximately 19 kD that increase significantly in amount in said conifer during fall season (autumnal) months and that increase significantly in amount in said conifer during fall season months and that is associated with seedlings having frost hardiness, and assessing frost hardiness based on said detected amount.

10. A kit for determining frost hardiness of conifer seedlings which develop a cold protein in fall months that is associated with protection of said seedlings against frost, comprising a supply of an antibody that binds to said cold protein, a developing agent for indicating the presence of said antibody and equipment for enabling a sample of said tissue from said seedling to be exposed to said antibody and detected.

* * * * *